United States Patent
Trbojevic

(10) Patent No.: US 9,095,705 B2
(45) Date of Patent: Aug. 4, 2015

(54) SCANNING SYSTEMS FOR PARTICLE CANCER THERAPY

(71) Applicant: Brookhaven Science Associates, LLC, Upton, NY (US)

(72) Inventor: Dejan Trbojevic, Wading River, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 14/099,061

(22) Filed: Dec. 6, 2013

(65) Prior Publication Data

US 2014/0163301 A1 Jun. 12, 2014

Related U.S. Application Data

(60) Provisional application No. 61/734,493, filed on Dec. 7, 2012.

(51) Int. Cl.
*G21K 5/04* (2006.01)
*A61N 5/10* (2006.01)

(52) U.S. Cl.
CPC ............. *A61N 5/1043* (2013.01); *A61N 5/1081* (2013.01); *A61N 2005/1087* (2013.01)

(58) Field of Classification Search
USPC ........... 250/396 R, 397, 398, 396 ML, 492.1, 250/492.3; 600/1; 315/500, 501, 502, 503, 315/504, 505
See application file for complete search history.

(56) References Cited

U.S. PATENT DOCUMENTS

| | | | |
|---|---|---|---|
| 4,870,287 A | 9/1989 | Cole et al. | |
| 5,260,581 A | 11/1993 | Lesyna et al. | |
| 5,585,642 A | 12/1996 | Britton et al. | |
| 7,345,291 B2 | 3/2008 | Kats | |
| 7,432,516 B2 | 10/2008 | Peggs et al. | |
| 7,582,886 B2 | 9/2009 | Trbojevic | |
| 8,173,981 B2 | 5/2012 | Trbojevic | |
| 8,426,833 B2 | 4/2013 | Trbojevic | |
| 2007/0262269 A1 | 11/2007 | Trbojevic | |
| 2010/0038552 A1* | 2/2010 | Trbojevic | ............... 250/396 ML |

OTHER PUBLICATIONS

D. Trbojevic et al., "Design of a Nonscaling Fixed Field Alternating Gradient Accelerator," Physical Review Special Topics—Accelerators and Beams 8.050101, pp. 050101-1-050101-10, May 19, 2005.

(Continued)

*Primary Examiner* — Nicole Ippolito
(74) *Attorney, Agent, or Firm* — Dorene M. Price

(57) ABSTRACT

A particle beam to treat malignant tissue is delivered to a patient by a gantry. The gantry includes a plurality of small magnets sequentially arranged along a beam tube to transfer the particle beam with strong focusing and a small dispersion function, whereby a beam size is very small, allowing for the small magnet size. Magnets arranged along the beam tube uses combined function magnets where the magnetic field is a combination of a bending dipole field with a focusing or defocusing quadrupole field. A triplet set of combined function magnets defines the beam size at the patient. A scanning system of magnets arranged along the beam tube after the bending system delivers the particle beam in a direction normal to the patient, to minimize healthy skin and tissue exposure to the particle beam.

20 Claims, 11 Drawing Sheets

(56) References Cited

OTHER PUBLICATIONS

R. Gupta et al.. "Test Results of HTS Coils and an R&D Magnet for RIA," Particle Accelerator Conference, Knoxville, TN, 3 pages, May 16-20, 2005.

D. Harding et al., "Magnet Design Issues and Discussion," Presentation at FFAG Workshop at Fermilab, 12 pages, Apr. 3, 2005.

R. Fuchs et al., "The Heavy Ion Gantry of the HICAT Facility," 3 pages, Publication Date Unknown.

B. Parker, "The Serpentine Coil Design for BEPC-II Superconducting IR Magnets," Presentation at IHEP/CAS, Beijing, P.R. China, 25 pages, Jan. 12, 2004.

K. Halbach, "Design of Permanent Multipole Magnets with Oriental Rare Earth Cobalt Material," Nuclear Instruments and Methods, 169, pp. 1-10, 1980.

R. Ueno et al., Multi-Orbit Synchrotron with FFAG Focusing for Acceleration of High Intensity Hadron Beams, Proceedings of the 1999 Particle Accelerator Conference, New York, pp. 2271-2273, 1999.

D. Trbojevic et al., "A Dramatically Reduced Size in the Gantry Design for the Proton-Carbon Therapy", Jun. 26-Jun. 30, 2006, 10th Biennial European Particle Accelerator Conference, 5 pages, Jun. 2006.

M. Kramer et al., "Treatment Planning for Heavy-Ion Radiotherapy: Physical Beam Model and Dose Optimization", Phys. Med. Biol. 45, cover page and 3299-3317, 2000.

E. Pedroni et al., "The 200-MeV Proton Therapy Project at the Paul Scherrer Institute: Conceptual Design and Practical Realization", Med. Phys. 22 (1), cover page and pp. 37-53, Jan. 1995.

J. Farr et al., "Clinical Characterization of a Proton Beam Continuous Uniform Scanning System with Dose Layer Stacking", Med. Phys. 35 (11), cover page and pp. 4945-4954, Nov. 2008 (published Oct. 14, 2008).

M. Phillips et al., "Effects of Respiratory Motion on Dose Uniformity with a Charged Particle Scanning Method", Phys. Med. Biol., vol. 37, No. 1, cover page and pp. 223-234, 1992.

D. Weber et al., "Spot Scanning Proton Therapy in the Curative Treatment of Adult Patients with Sarcoma: The Paul Scherrer Institute Experience", Int. J. Radiation Oncology Biol. Phys., vol. 69, No. 3, pp. 865-871, 2007.

T. Kanai et al., "Three-Dimensional Beam Scanning for Proton Therapy", Nuclear Instruments and Methods 214, pp. 491-496, 1983.

D. Miller, "A Review of Proton Beam Radiation Therapy", Med. Phys, 22 (11), Pt. 2, cover page and pp. 1943-1954, Nov. 1995.

A. Smith, "Vision 20/20: Proton Therapy", Med. Phys. 36 (2), cover page and pp. 556-568, Feb. 2009 (published Jan. 26, 2009).

T. Furukawa et al., "Design Study of a Raster Scanning System for Moving Target Irradiation in Heavy-Ion Radiotherapy", Med. Phys. 34 (3) cover page and pp. 1085-1097, Mar. 2007 (published Feb. 27, 2007).

D. Schulz-Ertner et al., "Effectiveness of Carbon Ion Radiotherapy in the Treatment of Skull-Base Chordomas", Int. J. Radiation Oncology Biol. Phys., vol. 68, No. 2, pp. 449-457, 2007.

M. Durante et al., "Charged Particles in Radiation Oncology", Nat. Rev. Clin. Oncol., vol. 7, pp. 37-43, Jan. 2010 (published online Dec. 1, 2009).

* cited by examiner

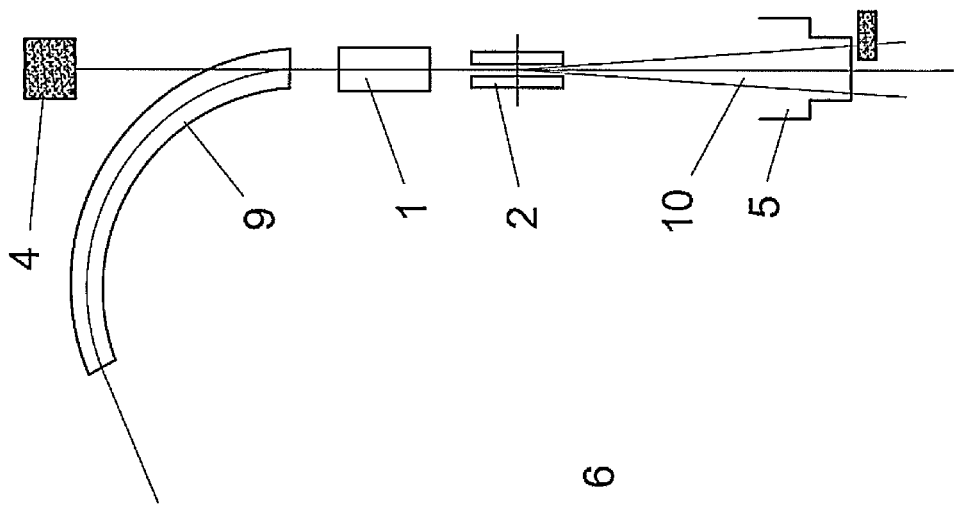
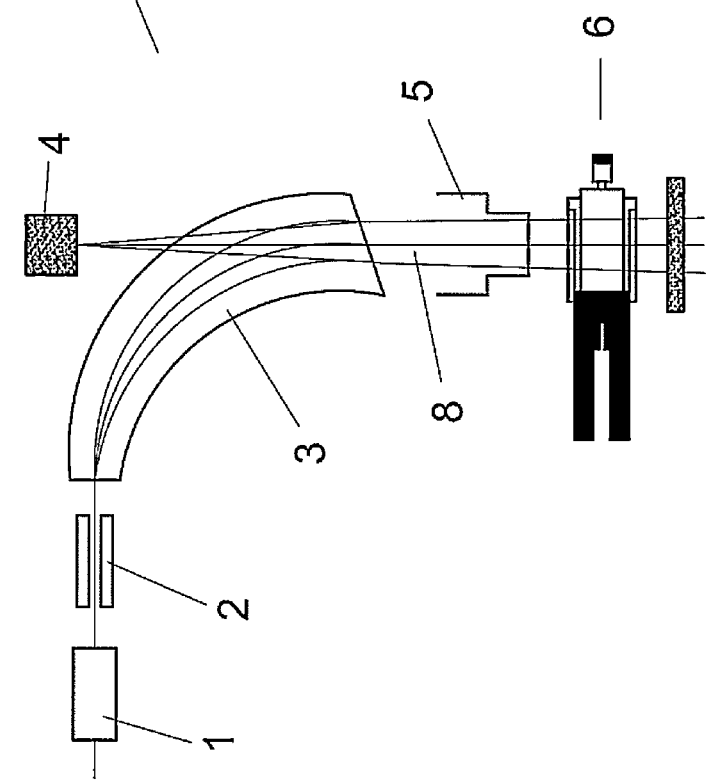
FIG.1B
FIG.1A

US 9,095,705 B2

SCANNING SYSTEMS FOR PARTICLE CANCER THERAPY

CROSS-REFERENCE TO RELATED APPLICATIONS

This application claims the benefit of U.S. Provisional Application No. 61/734,493 filed Dec. 7, 2012, incorporated herein by reference in its entirety.

STATEMENT OF GOVERNMENT LICENSE RIGHTS

This invention was made with Government support under contract number DE-AC02-98CH10886, awarded by the U.S. Department of Energy. The Government has certain rights in the invention.

BACKGROUND

The present invention relates generally to a medical cancer therapy facility and, more particularly, to a medical particle delivery system having a compact gantry design. Embodiments of the invention relate to apparatuses and methods for transfer scanning systems for use in cancer therapy.

Subject matter of the invention pertains to methods and apparatus for using, generating, controlling or detecting radiant energy, that is, energy propagated in the form of electromagnetic waves, or traveling subatomic, atomic or molecular particles, combinations and subcombinations including such methods or apparatus, and accessories therefore. In a medical setting, a cancerous object or other invasive material is irradiated by a stream of particles, generated in a medical synchrotron, for example, and delivered to a patient by way of a beam gantry. Medically-useful particles may include protons, neutrons, and atomic nuclei, such as those of tritium and carbon.

It has been known in the art to use a particle accelerator, such as a synchrotron, and a gantry arrangement to deliver a beam of particles, such as protons, from a single source to one of a plurality of patient treatment stations for cancer therapy. In such systems, the cancerous tumor will be hit and destroyed by particles in a precise way with a localized energy deposition.

Hadron cancer therapy facilities deliver particle beam energy localized in a patient's body. The beam energy is conformed to fit a targeted volume, such as a cancerous tumor. The beam energy is conformed to a tumor volume in three dimensions using two systems: A scanning system sweeps the beam to cover a tumor area, while a beam-energy control system modulates the energy level of the beam to determine dose depth, or longitudinal penetration, based on the Bragg-peak developed by the particle beam. Dose penetration is spanned using a range of beam energies, whereby the sharp Bragg peak characteristic of a mono-energetic beam can be widened, so that the depth of a tumor can be fathomed. The widened Bragg peak may be referred to as a spread-out Bragg peak (SOBP). Combined, transverse scanning and SOBP are employed to dose a tumor volume. In this way, radiation damage to healthy cells is dramatically reduced in comparison to other radiation treatments using photons (X and Gamma rays) or electrons, for example, which pass through the tumor to be treated, as well as through intervening and subsequent tissue.

Ion therapy is similar in concept to external beam radiation therapy—the idea is still to target and kill tumor cells by destroying their haywire DNA, but particle beams have properties that make them ideal for cancer therapy. The particle radiation therapy is done in 2 steps: 1) a three dimensional reconstruction of the tumor and its relationship to the surrounding structures and 2) a reproducible treatment position that minimizes movement errors. Initially, the scans are done by using tomography scans (CT) for region of interest and slices are determined in 2 to 3 millimeter intervals. The regions of interest are identified and marked for irradiating the tumors by a physician. Physicists and dosimetrist create a treatment plan by using a computer model that determines a series of angles and beams through the tumor. A medical doctor then reviews the plan. The treatment beams are also conformal beams shaped to the three-dimensional tumor.

Particle radiation treatment may be done by a scanning technique, such as single beam scanning and pencil beam scanning. Single beam scanning, also known in the art as uniform scanning, uses magnets to scan a broad beam across a treatment field. This type of scanning typically uses collimators to shape the beam. Collimators are large metal pieces that are carved out of beam-blocking or beam-absorbing metals, and directly shape the beam. Pencil or spot beam scanning is used to irradiate a tumor transversely, scanning across from the left to right and from top to bottom. The transverse beam spot scanning is done with the beam at a specific energy. A computer and device are programmed to carry out the method of transverse beam scanning by sweeping the beam in successive depth-layers of the tumor, reaching the extent of the tumor in the X-Y plane at each specific depth. The transverse scanning then moves to the next layer when the beam energy is changed, accordingly. Fast scanning magnets move the beam spot in X-Y direction, while quadrupole triplet magnets define the beam spot size at the patient.

Proton and carbon therapy facilities include an injector providing a beam from, starting from an ion source to an accelerator, and transport and delivery systems. The gantry delivery systems for proton and especially carbon ions typically are the most expensive part of any treatment facility. Delivery systems include a large bending magnet at the end as the scanners are placed before them. Apertures of the large bending magnets have to allow for beam motions on the order of +/−10 cm. Even in the case of proton therapy, which is a smaller device, the proton therapy device weighs with the magnets a minimum of 40 tons.

The gantry of a typical particle beam cancer therapy system accepts a particle beam of a required energy from the accelerator and projects it with high precision toward a cancerous tumor within a patient. Ions are accelerated by an accelerator and are shaped for delivery by a gantry. The ion particle energy is determined within the accelerator to allow their energy to be deposited in the tumor cells. The beam from an isocentric gantry must be angularly adjustable so that the beam can be directed into the patient under different angles of entrance. This flexibility is necessary to avoid radiation to the sensitive healthy organs or spine. Because of these requirements, the gantry of a conventional particle beam cancer therapy facility is typically the most expensive piece of equipment of the treatment facility and its magnets are generally very large and heavy.

For example, the proton-carbon medical therapy facility described by R. Fuchs and P. Emde in "The Heavy Ion Gantry of the HICAT Facility" includes an isocentric gantry system for delivery of protons, Helium, Carbon and Oxygen ions to patients. The gantry system has a total weight of 630 tons and the required beam line elements for transporting and delivering fully stripped Carbon and Oxygen ions with 430 MeV/nucleon kinetic energy have a total weight of 135 tons. The rotating part of the isocentric gantry system weighs about 570 tons due to its role to safely transport and precisely deliver ions to the patients. This extreme weight results in significant amount of structural cost for a building that can support this massive rotating gantry weight.

Further, another system, which is different than the present invention, is the Paul Scherrer Institute (PSI) proton therapy facility that contains a scanning method before entering into the dipole magnets. This technique performs the scanning prior to the bending of the particles. Specifically, the PSI proton facility bends protons in a large 40 tons dipole magnet. There is a need for a small gantry system that provides the same treatment options to a patient.

Further, a Source to Axis Distance (S.A.D.) defines the angle of arrival of a beam to a patient's skin. The optimal condition is a normal angle with beam spots which are parallel to each position, such that S.A.D.=∞. That is, the S.A.D. is preferred to be as large as possible. In a path toward gantry size reduction, a condition that creates a normal angle of incidence to the patients should not be abandoned.

U.S. Pat. No. 7,582,886, issued Sep. 1, 2009, U.S. Pat. No. 8,173,981, issued May 8, 2012, and U.S. Pat. No. 8,426,833, issued Apr. 23, 2013, all to Trbojevic, relate to medical particle therapy gantries, and are incorporated herein by reference in their entireties. U.S. Pat. No. 7,432,516 issued Oct. 7, 2008, to Peggs, et al., relates to rapidly cycling medical synchrotrons and beam delivery systems, and is incorporated herein by reference in its entirety.

SUMMARY OF INVENTION

The present invention pertains to a particle-therapy gantry and methods for delivering beam particles to a patient. Such a gantry may be used, for example, in a hadron cancer therapy facility. The present invention also pertains to a cancer therapy system that includes the particle-therapy gantry and a particle beam accelerator. Preferably, the particle beam accelerator is a fast cycling synchrotron, and gantry magnets operate synchronously with the synchrotron to provide particles at energy levels corresponding to dosage targeting depths.

An ion beam to treat malignant tissue is delivered to a patient by a gantry. The gantry includes a beam tube dimensioned for use in a treatment room to deliver a particle beam to a patient, the beam tube defining a particle beam path with a particle beam entry point and a particle beam exit point. The beam tube may be made up of discrete beam-tube sections.

A transfer system of a plurality of small magnets is arranged sequentially along the beam tube to transfer the particle beam from the particle beam entry point with strong focusing and with a small dispersion function, such that a beam size in the transfer system is very small, thereby allowing for the small size of the magnets.

A bending and focusing system of magnets arranged along the beam tube in the transfer system of magnets, uses the property of combined function magnets where the magnetic field is a combination of the bending dipole field with a focusing or defocusing quadrupole field. A set of three combined function magnets defines the beam size at the patient, at the end of a transport part of the gantry.

A scanning system of magnets arranged along the beam tube after the bending system and before the particle beam exit point delivers the particle beam from the particle beam exit point to the patient in a direction normal to the patient, thereby minimizing exposure to the ion beam of healthy skin and tissue. The scanning system of magnets includes a first scanning magnet and a second scanning magnet. The first scanning magnet is a small aperture magnet, and the second scanning magnet is a large-aperture magnet. The second scanning magnet delivers the particle beam in a direction normal to the patient. Advantageously, the present invention obviates the need for the very large magnets at the end of the gantry, in contrast to other operating existing gantries.

A particle beam therapy system includes a source of particles, an accelerator for accelerating the particles to desired energy levels, and an injector for transporting the particles from the source to the accelerator. A patient treatment room in a typical system installation includes a rotatable gantry for delivering a beam of the accelerated particle to the patient.

DESCRIPTION OF THE DRAWINGS

These and other features, aspects, and advantages of the present invention will become better understood with regard to the following description, appended claims, and accompanying drawings where:

FIGS. 1A and 1B are an illustration of two prior art gantry systems;

DETAILED DESCRIPTION

Figure 2:
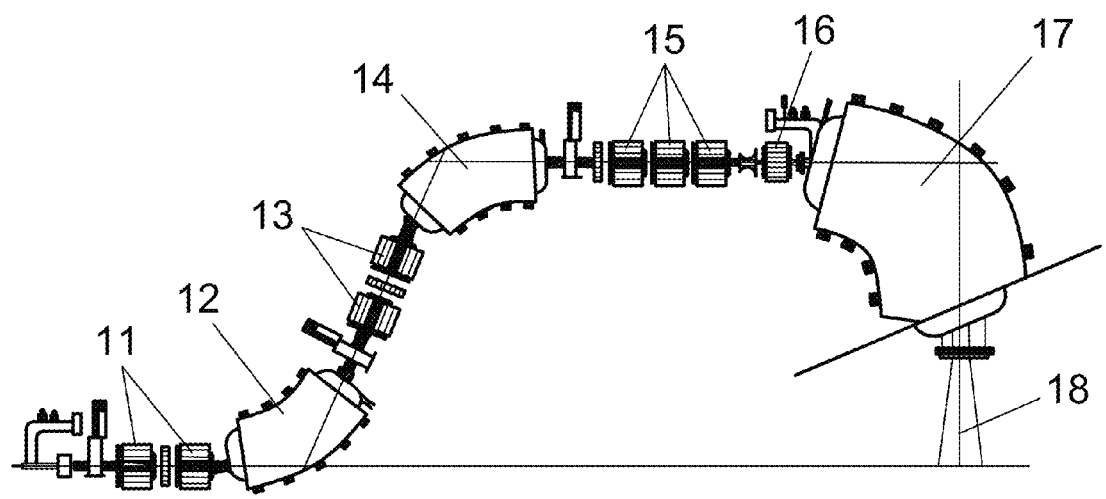
FIG. 2 is an illustration of a further prior art gantry system, located in Switzerland at the Paul Scherrer Institute (PSI), that contains triplet quadrupoles magnets placed before the scanning system and a large magnet used to bend the beam 90° degrees.

Referring initially to FIGS. 1A and 1B, illustrated are two prior art scanning solutions, with gantries shown in side view. In FIG. 1A at the left side shows one plane scanning magnet 1, a scanning magnet 2, a large bending magnet 3, an X-ray tube 4, a schematic presentation of the nozzle 5, a patient 6, below the nozzle 5, and the shielding below the patient 6. The emphasis is on parallel beam 8 directed towards the patient 6. On the right hand side in FIG. 1B, a plane scanning magnet 1 and a scanning magnet 2 are positioned downstream of a smaller bending magnet 9. A particle beam 10 may be directed toward a patient via the nozzle 5. The beam arrives to the patient with angles defined by the distance between the scanning magnet and the patient 10 and a loss of parallel beam condition.

FIG. 2 illustrates a prior art gantry system at the PSI. The PSI gantry system contains first doublet quadrupoles 11, first bending dipole 12, second doublet quadrupoles 13, second opposite bending dipole 14, third triplet quadrupoles 15, scanning magnets 16, and third bending magnet 17. Proton beam arrives to the patient with angles very close to the normal 90°, as the third bending magnet 17 provides double focusing point at the patient. These components are currently being used and are large and heavy; therefore the present invention described below illustrates an improved compact treatment therapy device.

Figure 3:
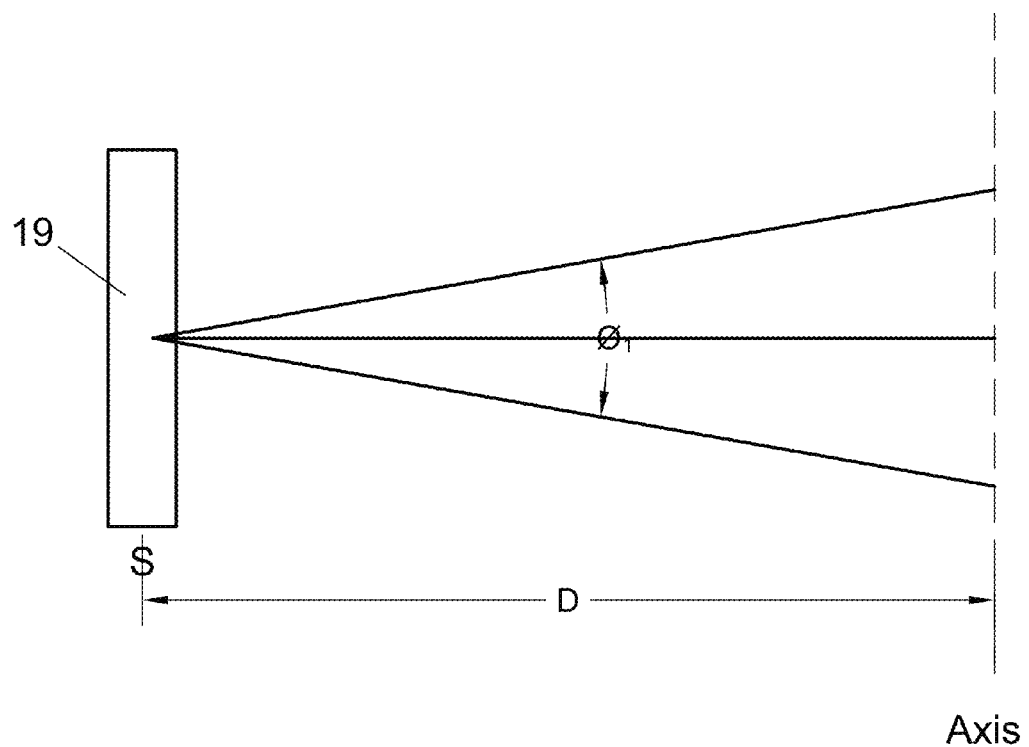
FIG. 3 is an illustration of the source to axis distance definition (S.A.D.), which is the starting point of examination of the spot scanning that shows the source point at "S", direction of the beam to the patient (labeled Axis), angles of the beam, and the Δ Of the arrival target depending on the distance "D"

Referring now to FIG. 3, illustrated is a definition of the Source to Axis Distance (S.A.D.). The source point 19 represents the center of the scanning magnet. The larger the bending angle of the scanning magnet the larger the delivery angle $\theta_1$ to the patient. Axis in FIG. 3 represents the position of the patient. A goal of the present invention is to reduce the delivery angles to allow beam delivery more normal to the patient. Normal angles of particle beam incidence minimize exposure of patient tissue in treating tumors, because a particle beam arriving normal to a patient's skin and directed at a tumor will travel the shortest distance through intervening tissue to arrive at the target.

Figure 4:
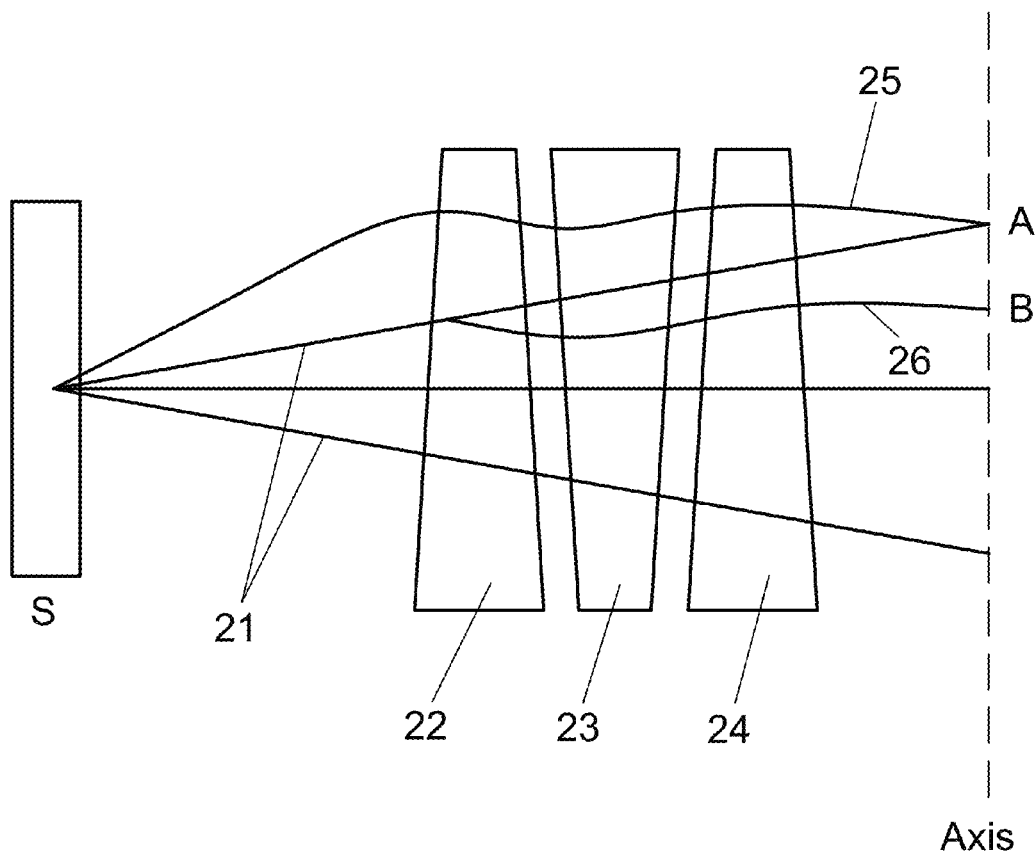
FIG. 4 is an illustration of how to create a normal angle of incident to the patient, and showing a normal angle of incidence being distorted by three large aperture combined function magnets.

Referring now to FIG. 4, illustrated is an initial attempt to obtain the normal angle of incidence to the patient. The two beam directions, beam rays 21, show the source to axis distance (S.A.D.) condition from FIG. 3. The beam rays 21 are passed through three combined function magnets. The functional magnets are: the horizontally focusing (F) and bending magnet 22, the horizontally defocusing (D) and bending magnet 23, and last triplet, a horizontally focusing (F) and bending combined function magnet 24.

Effects of these magnets on the beam ray orbit 21 with respect to the beam arrival to the patient are explained. The horizontally focusing F magnet 22 bends the beam towards the central line normal to the patient, which allows wider angle beams to be focused into the center; the horizontally defocusing D magnet 23 deflects the beam outward of the central line normal to the patient, which is used to guide the beam in the correct horizontal plane; the triplet horizontally focusing F magnet 24 sends the beam under an angle of 90° to the patient reaching the point B on the beam path 26, which this magnet is used to straighten the beam out and allow the beam to reach its specific point of interest. To reach the same transverse distance at the patient "A," as previously with only one scanning magnet, a new beam path 25 is required. This almost doubles the value of the scanning magnet kick but the final result is a normal angle of incidence to the patient. However, the new beam path 25 may result in large values of the horizontal and vertical apertures for all three combined functional magnets. The present invention solves the problem by supplying a scanning system after bending the beam.

Embodiments of the present invention may reduce the size of the delivery system required for the patient. Embodiments encompass the use of the three combined function magnets, previously shown with the scanning magnet placed before the last combined function magnet and then adding an additional scanning magnet downstream. Embodiments include placing both scanning magnets downstream of all the gantry magnets above the patient. Embodiments of the invention may also improve the transverse scanning system allowing an infinite value for S.A.D.—(beam arrives always under the normal angle to the patient skin with beam spots parallel to each other) but without the need for large bending magnets. This approach reduces overall weight of the isocentric gantry and provides optimum conditions for beam arrival to the patient. The beam size delivered to the patient is defined by the combined function magnets placed before the scanning system. The additional scanning magnet downstream further distinguishes the embodiments of the invention from the prior art. The second scanner follows the same scanning function of the first scanner but bends in an opposite direction. The combination of first scanning and second scanning magnets provides for a normal angle of incidence. Both scanning magnets are placed above the patient. The second scanning magnet may have a large aperture as ±10 cm beam offsets are required in both x and y transverse planes. The large aperture is advantageous for treating large tumors such as those, which frequently occur in the lungs.

Figure 5:
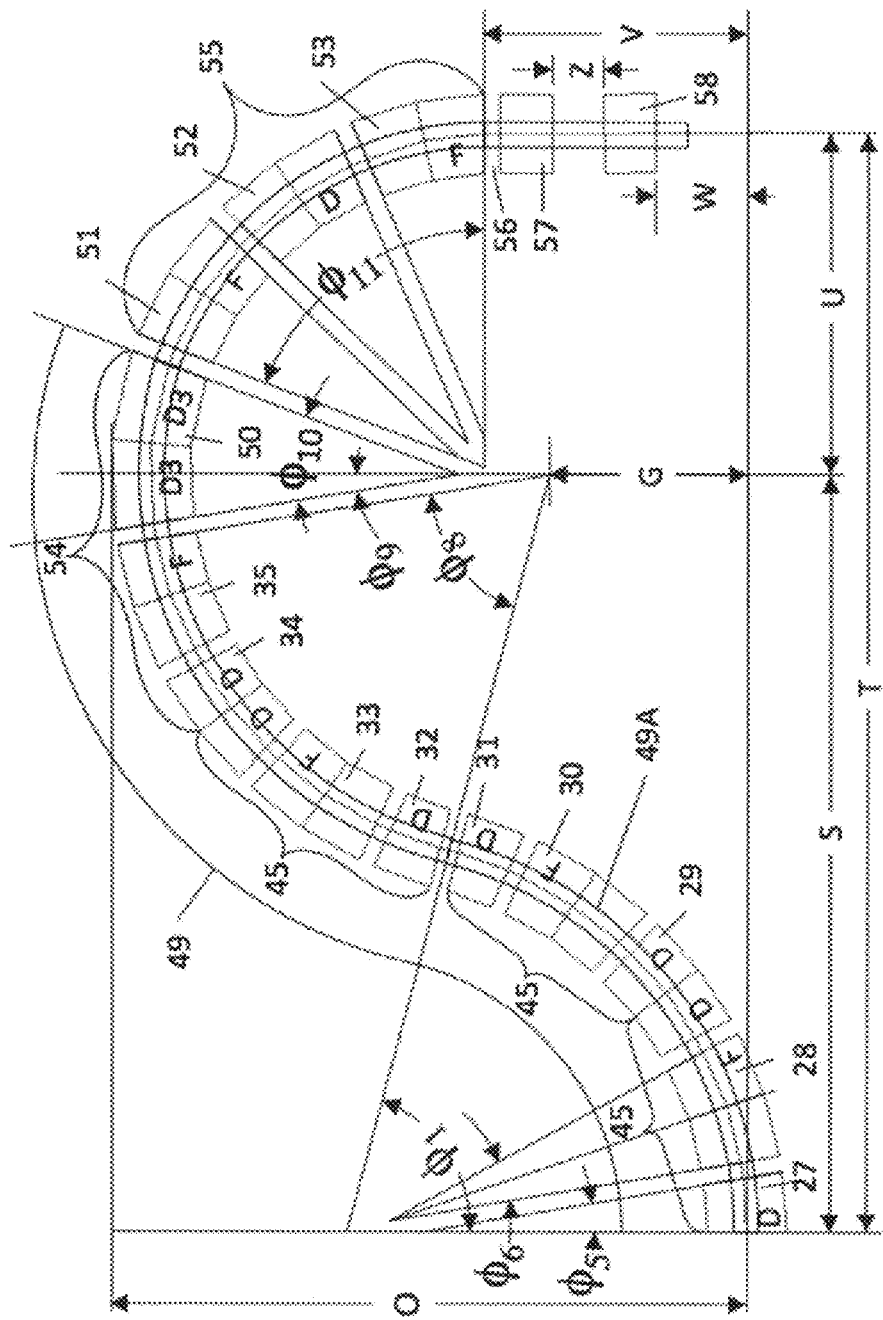
FIG. 5 is an exemplary illustration of a proton isocentric gantry optimized gantry with a scanning system at the end of the gantry, according to the present invention, without multiple large aperture magnets.

FIG. 5 is an exemplary illustration of the optical components of the gantry 49. The gantry 49 generally includes a hook-shaped beam pipe 49A, the beam pipe 49A corresponding to a beam tube defining a particle beam path for delivery of a particle beam to a patient and includes a series of identical fixed-field magnet triplets 45 and 54 arranged in sequence around the beam pipe. The beam pipe 49A can be provided as a continuous pipe, or it can be assembled from a plurality of beam pipe segments welded or otherwise fastened together in a conventional manner. The beam tube corresponding to the beam pipe 49A defines the particle beam path, the particle beam path being indicated generally by the "line" extending along and through a center the beam pipe 49A in the transport system illustrated in FIG. 5. Also, the beam tube defines the particle beam path to transport the particle beam from a particle beam entry point at which the particle beam enters the beam tube to a particle beam exit point at which the particle beam exits the beam tube. The fixed combined function magnets 45 are made of three magnets: half of a defocusing magnet 27, a focusing magnet 28, and half of a defocusing magnet 29, as described in U.S. Pat. No. 8,173,981, incorporated herein by reference. The gantry starts with a half-length, combined-function, defocusing magnet 27. Bending of the beam upwards starts with a plurality of triplet magnets 45. The triplet magnets 45 are composed of defocusing and focusing magnets. First set of two identical triplets magnets 45 make up the angle $\Phi_1$ of about 75° degrees bending angle. The full lengths of the defocusing and focusing magnets are $L_D$=62 cm and $L_F$=68 cm, respectively. The maximum dipole components, at proton energy of 250 MeV, of the defocusing and focusing combined function magnets are $B_{yD}$=1.283 T and $B_{yF}$=1.17 T, respectively; their gradients are $G_D$=−9.684 T/m and $G_F$=+8.565 T/m, respectively. Bending angles of both defocusing and focusing magnets are the same $\Phi_D$ and $\Phi_F$, and a bending angle $\Phi_6$ being about 18.75° degrees, with a bending angle $\Phi_5$ being also illustrated. The magnetic steel with a different shape of each magnet is placed close to the next magnet. The effective distance is 8 cm, and the same copper coil is used for all magnets. The first set of two triplet magnet 45 also include the magnet 30 and are finished with a half-length defocusing magnet 31. Benefits of the first set of triplet magnets include the reductions in energy and size since the bending of the angle $\Phi_1$ is about 75°, which allows for a series of smaller bending magnets as opposed to a single large bending magnet.

The third set of triplet magnets 45 includes the magnet 33 and starts with a defocusing combined function magnet 32, which starts to bend the particles in the opposite bending direction and finishes with a half defocusing magnet 34. A triplet set of combined function magnets 54 starts with a half defocusing magnet 34, continues with a focusing combined function magnet 35, and finishes with a defocusing magnet D3 that is a first half of full defocusing magnet 50 having a bending angle $\Phi_{10}$ of about 30 degrees, and the angles $\Phi_8$ and $\Phi_9$ are also associated with the triplet set of combined function magnets 54, as illustrated in FIG. 5.

Following the triplet combined function magnets 54 is a set of directional triplet bending magnets 55, which bend the beam toward the patient. The directional triplet bending magnets 55 as a whole also function to define the spot size of the beam, directed towards the patient. The bending magnet series 55 is made up of combined function magnets 51, 52, and 53. The combined function magnets 51, 52, and 53 are of the same length of 56 cm and the same bending angle of $\Phi_{11}/3$ of about 52°/3 degrees. The dipole magnetic field is $B_{TRIPLET}$ and is about 1.32 T. The triplet gradients are to be adjusted for different spot sizes. In an exemplary embodiment, the spot size was selected to be σ=0.32 mm (3.29 $\sigma_{98\%}$=1 mm), by defining a value of the betatron function of β*=1 m at the patient.

A scanning system follows the directional triplet bending magnets 55. A first scanning magnet 57, has a maximum dipole magnetic field of $B_{SC1}$=±0.73 T (the field is required for the protons with maximum kinetic energy of 250 MeV and to provide for the maximum transverse distances of ±10 cm– (bending angle of 0.0903 rad)). A second, large aperture scanning magnet 58 brings the beam to a normal angle of incidence to the patient.

A gantry total length, which is defined as T, for the projection to the horizontal axis is equal to T=6.367 meters, or can range from 6 meters to 8 meters. A vertical distance of delivery W, which is between the patient and the second scanning magnet 58 is equal to W=0.73 m, and, roughly can be extended between W=0.5 in to 1.5 m. A distance between the last magnet of the transport part of the gantry and the beam spot triplet magnets is between 9 cm-12 cm, with a distance between the combined function magnet 53 and the first scanning magnet 57 being indicated by the numeral 56. Also, for example, the height "O" of the gantry is O=3.40 meters, a horizontal projection "S" from the beginning of the gantry 49 to a central position where the height is largest is equal to S=4.42 meters, with a range of 4 meters-6 meters, with "U" being a remaining distance of the gantry total length "T". A vertical distance "G" extends from a location corresponding to endpoints of the distances "S" and "U" at a location from a patient to the first scanning magnet 57, a vertical distance "V" extends between the patient to the last triplet magnet 53 of V=1.49 meters, and a distance "Z" extends between the first and second scanning magnets 57 and 58 of Z=30 cm. The dimensions described in connection with FIG. 5 are only provided to illustrate a range length when physically constructed.

Figure 6:
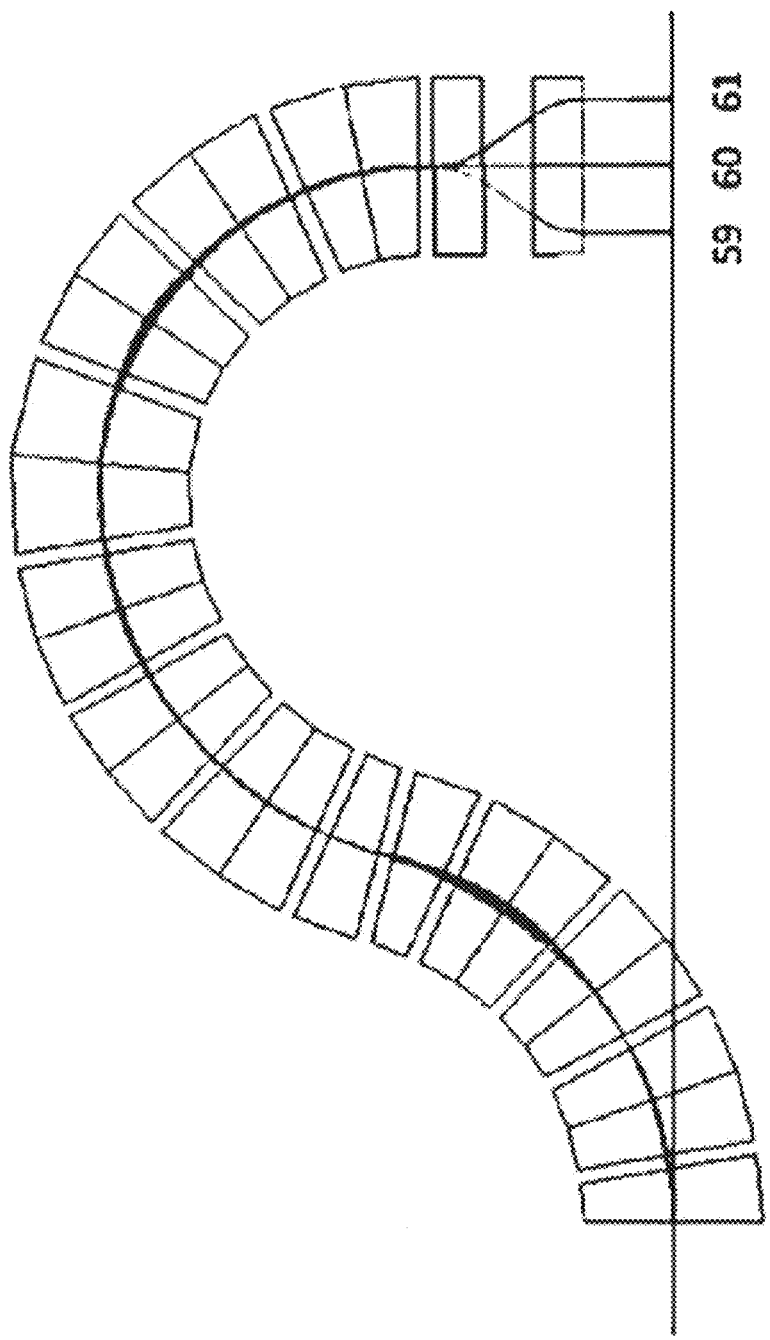
FIG. 6 is an exemplary illustration of an optimized proton gantry with the scanning system turned on according to the present invention, with three beam positions.

Referring now to FIG. 6, shown is a path of an ion beam through the gantry. The FIG. 6 is not necessarily drawn to scale, and the position and dimensions of the ion beam may be exaggerated for illustration purposes. Three transverse positions are shown: a negative beam offset 59, a zero beam offset 60, and a positive beam offset 61. The zero beam offset 60 represents a scenario where both scanning magnets 57 and 58 in FIG. 5 are turned off. According to embodiments of the invention the offset may be varied in any distance between about 0 cm and +/−10 cm by controlling the scanning magnets appropriately. In certain embodiments the offset may be varied in any distance between about 0 cm and +/−10 cm. The range of ±10 cm may also be achieved by the difference in distance between the magnets. The further the magnets are from the patient the easier it is to bend the beam. In an exemplary embodiment, the second scanning magnet 58 has a large aperture. For example, the second scanning magnet has an aperture of 12 cm+/− and bends the ion beam in the opposite direction of the first scanning magnet to achieve an optimal incidence delivery angle.

Figure 7:
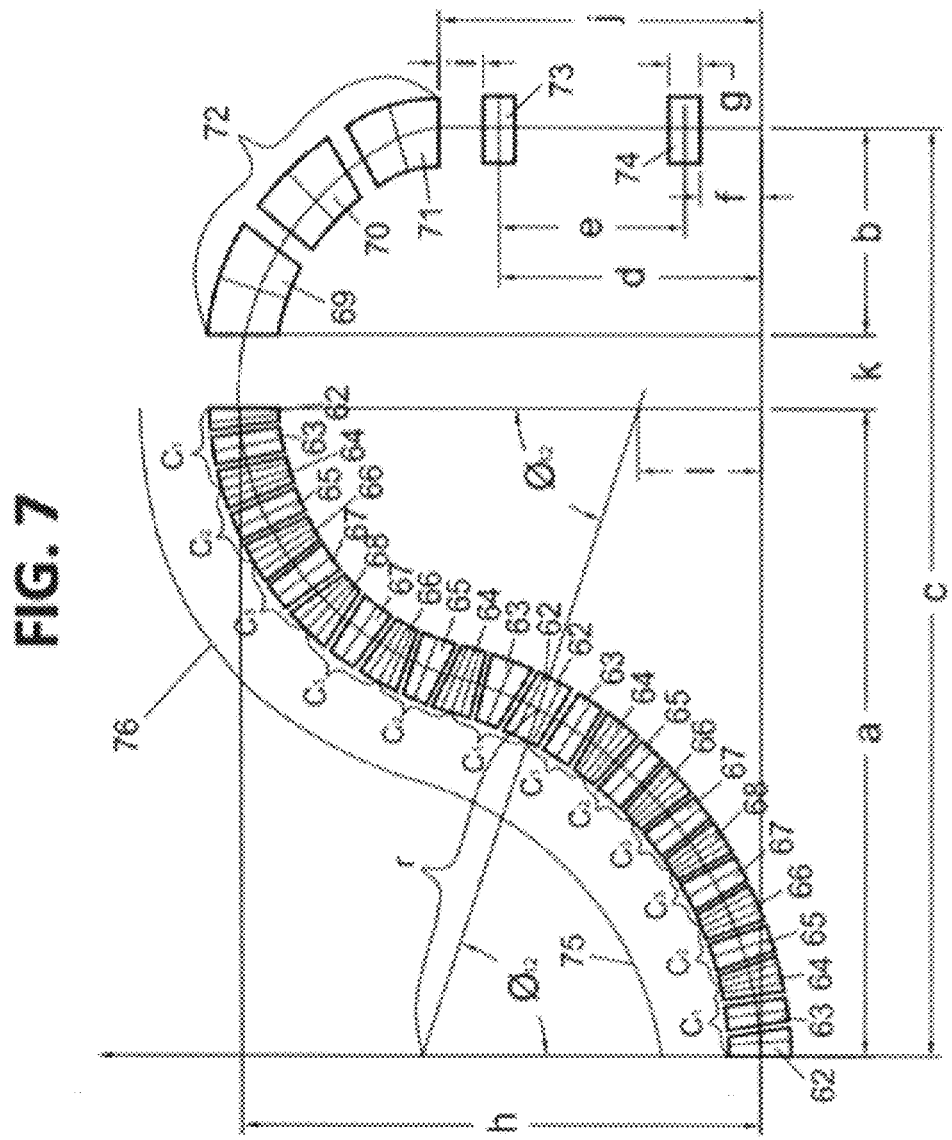
FIG. 7 is an exemplary illustration of an ion (carbon-proton) isocentric optimized gantry according to the present invention with the scanning system at the end of the gantry.

Referring now to FIG. 7, there is illustrated a carbon ion gantry according to an exemplary embodiment of the present invention, built using superconducting combined function magnets. The beam tube defines the particle beam path to transport the particle beam from a particle beam entry point at which the particle beam enters the beam tube to a particle beam exit point at which the particle beam exits the beam tube, the particle beam path being indicated generally by the "line" extending along through the transport system illustrated in FIG. 7. A first magnet 62 is half of a defocusing superconducting combined function magnet with a length of $L_{D^{1/2}}$=13 cm, while the full length is $L_D$=26 cm. The dipole magnetic field is $B_D$=4.55 T, while the gradient is $G_D$=−90 T/n. A next focusing combined function magnet 63 is focusing with opposite bending with a dipole magnetic field of $B_F$=−0.385 T, and a focusing gradient of $G_F$=+150 T/m. The length of the focusing magnet 63 is $L_F$=20 cm. The defocusing combined function magnet bending angle is $\theta_D$=0.1119997 rad or in angle range of 6°-7° while the focusing combined function magnet bending angle is in opposite direction $\theta_F$=−0.0145997 rad or in an angle range of 0.8°.

The total magnetic field in the defocusing magnets 64, 66, and 68, is at the orbit offset of the beam, at the specific energy. Further, for the focusing magnet, the magnetic field in the focusing magnets 63, 65 and 67 is equal to the sum of the dipole magnetic field and that of the orbit offsets of the carbon ions multiplied by the focusing gradient. The beam orbit has zero offsets at the central kinetic energy of MeV/u. The maximum values of the magnetic field in the defocusing magnet $B_D$=4.55 T, while in the focusing magnet $B_F$=−0.385 T. At the minimum kinetic energy of 218 MeV/u the offsets can reach up to or at least −/+7 mm, while for the maximum kinetic energy of 400 MeV the offsets can reach +9.5 mm. This makes the maximum magnetic field for the lowest energy range equal to: $B_{DTOT}$=4.55+(−90)*(−0.012)=5.63 T and for the maximum kinetic energy of 400 MeV/u $B_{DTOT}$+=4.55+ (−90)*(+0.010)=3.65 T. The focusing magnet has larger beam offsets at a minimum and a maximum energy range: at the minimum kinetic energy 218 MeV/u $X_{max}$=±0.013 m and at the maximum kinetic energy of 400 MeV/u $x_{max}$=−0.013 m with $X_{max}$=±0.020 meter. The maximum magnetic field for the lowest kinetic energy is $B_{FTOT}$=−0.385+150*(±0.013)=− 2.335 T or for the xmax=+0.013 the magnetic field is $B_{FTOT}$=1.565, while for the maximum kinetic energy of 400 MeV/u the maximum orbit offsets are $x_{max}$=±0.020 meter. The magnetic field for carbon ions at the focusing combined function magnets is $B_{FTOT}$=−0.385+150*(±0.020)=−3.4 T or for the case of $x_{max}$=+0.020 meter the maximum field for the fully stripped carbon ions is $B_{FTOT}$=−0.385+150*(0.020) =2.62 T. As the maximum orbit offset may be up to 20 mm, the required aperture radius should be $r_{min}$≥0.026 meters. The required gradient for the focusing magnet is 150 T/m, so the magnetic field at the superconducting coil radius of 0.030 m is G*r=B=150*0.030=4.5 T.

The next magnet 64 is a half defocusing combined function magnet. This magnet defines the first cell $C_1$. The second cell $C_2$ starts with the same half length defocusing magnet 64; in other words, a 26 cm defocusing magnet 64 connects both artificially made cells $C_1$ and $C_2$. The remaining two combined function magnets 65 and 66, in the second cell $C_2$ are of different gradient magnets $G_{F2}$=167 T/m and $-G_{D2}$=−78 T/m. Again the last magnet of the second cell $C_2$ is a half defocusing magnet 66. The magnet 66 connects to cells $C_2$ and $C_3$. Next, the defocusing magnet 66 is connected in the beginning of the third cell $C_3$. The third cell also contains a focusing combined function magnet 67 and a defocusing magnet 68, which is the center of the first part series 75, the first part series 75 being associated with an angle $Ø_{12}$. The third cell $C_3$ finishes with the defocusing magnet 68. Again, the defocusing combined function magnet 68 belongs to two identical cells $C_3$, which is the end of one cell and the beginning of another cell.

From the center of the defocusing magnet 68 the gantry is mirror symmetric and the cells repeat until the bending upward is finished. Specifically, cell $C_3$ is connected to $C_2$, and again $C_2$ is connected then again to $C_1$. Further, the first cell $C_1$ is 13 cm long half of the defocusing combined function magnet. The next set of elements for the focusing and defocusing magnets is the second part series 76, the second part series 76 being associated also with an angle $Ø_{12}$. The next element 62, in the second part series 76, is the same defocusing combined function magnet 62, in the first part series 75, but with the opposite bending. The gradients in all opposite bending combined function magnets of the second part series 76 of the isocentric gantry are equal to the corresponding magnets in the first part series 75 of the gantry. For example, the gradient of the combined function magnet 67, is identical to the gradient of the combined function magnet 67, which is in the first part series 75. The first part series 75 and the second part series 76 of the isocentric gantry have a height of h=4.091 meter.

Then, a set of triplet condensed magnets 72 follows the second part series 76 of the isocentric gantry. A first magnet 69, in the triplet condensed magnets 72, is a 60 cm focusing combined function magnet with the bending field of $B_{FT1}$=4.615 T and gradient of $G_{FT1}$=22.3 T/m; follows a second magnet 70 with a length of 65 cm as a defocusing combined function magnet with the dipole field of $B_{DT2}$=4.261 T and a gradient of $G_{DT1}$=−16.05 T/m; last, a third bending magnet 71 in the triplet condensed magnets 72 is the 60 cm long focusing combined function magnet with the same dipole field as the first one: $B_{FT3}$=$B_{FT1}$=4.615 T, while the gradient is $G_{FT3}$=11.01 T/m.

This system further contains two scanning magnets 73 and 74 placed after the triplet-condensed magnets 72. The scanning system is made up of two horizontal/vertical bending magnets, the scanning magnets 73 and 74, following the triplet-condensed magnets 72. A distance between the triplet condensed magnets 72 and the first scanning magnet 73 is "i"=30 cm. The first scanning magnet 73 is "g"=30 cm long; and, the magnetic field is equal to $B_{SC1}$=±1.35 T, to produce the ±10 cm in both planes, for the maximum carbon ion kinetic energy of 400 MeV/u.

The second scanning magnet 74 is 1.257 meters away from the first scanning magnet 73, or their bend centers are equal to "e"=1.586, and the bend center of the first scanning magnet 73 is positioned above the patient at a distance "d". The second scanning magnet 74 is placed for "f"=0.5 m above the patient, and it requires opposite bending of the same strength as the first one to accommodate for an exact normal angle of incidence. The first scanning magnet 73 and second scanning magnet 74 are designed to direct the particles. The first scanning magnet 73 could be placed inside of the cryostat of the superconducting triplet magnets, but the second scanning magnet 74 has to be a warm magnet, which means it has to be outside the cryostat and with a large aperture: ±12 cm. It has to have a rectangular shape to allow scanning in two planes. This is the only large aperture magnet in the whole gantry system.

The height of the carbon gantry is equal to "h"=4.091 meters. The length of the projection to the horizontal axis is equal to "c"=7.672 m, with a distance "k" between an end of the second part series 76 of the isocentric gantry and an end of the triplet condensed magnets 72, and a distance "b" being included in the length "c". The average bending radius of the gantry is "r"=2.96 m. The height of the central bending point is "l"=1.1325 m, while a distance between the edge of the last triplet 71 to the patient is equal to "j"=2.6586 m. The length of the gantry elements 75 and 76 projection to the horizontal axis is "a"=5.63 m, while the average radius of the triplet 72 bending is b=1.432 meter, making the average bending dipole field equal to 4.43 T. The dimensions are only provided to illustrate a range length when physically constructed; however, the construction of the range can differ from that described.

Figure 8:
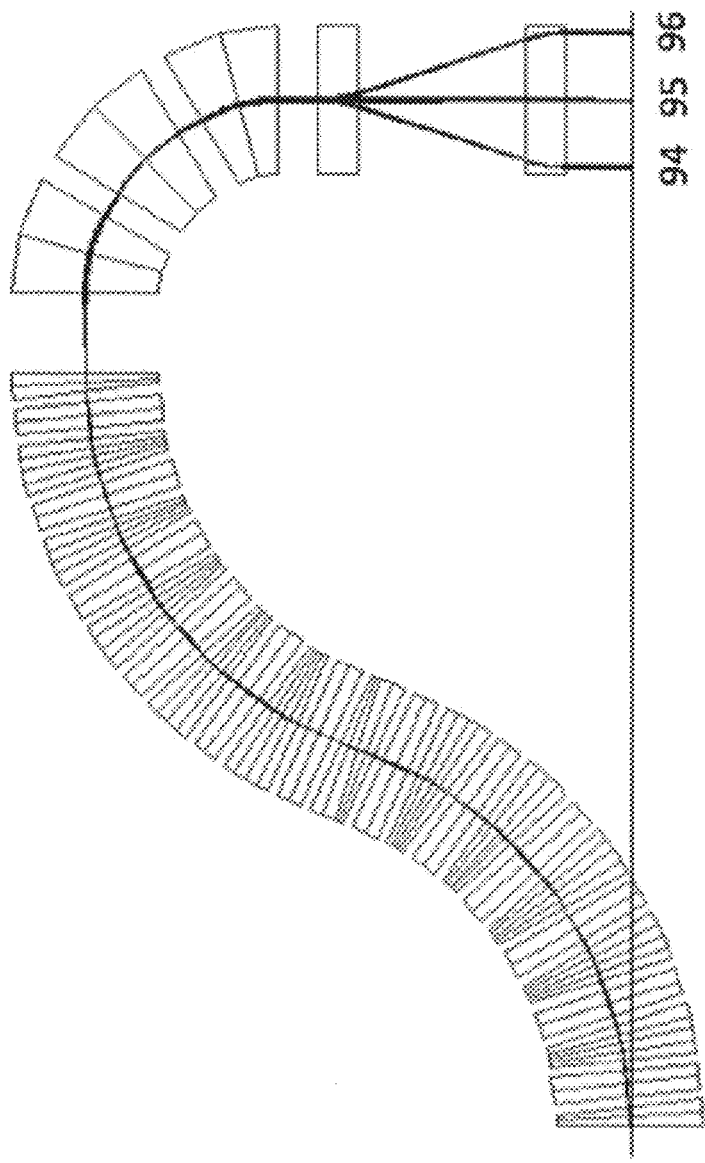
FIG. 8 is an exemplary illustration of the ion (carbon-proton) optimized gantry of the present invention with the scanning system turned on that shows three beam positions.

Referring now to FIG. 8, shown is a path of a carbon beam through the gantry of FIG. 7. The FIG. 8 is not necessarily drawn to scale, and the position and dimensions of the ion beam may be exaggerated for illustration purposes. Three transverse positions are shown: a negative beam offset 94, a zero beam offset 95, and a positive beam offset 96. The zero beam offset 95 represents a scenario where both scanning magnets 73 and 74 are turned off. According to embodiments of the invention the offset may be varied in any distance between about 0 cm and +/−20 cm by controlling the scanning magnets appropriately. In certain embodiments the offset may be varied in any distance between about 0 cm and +/−10 cm.

Figure 9:
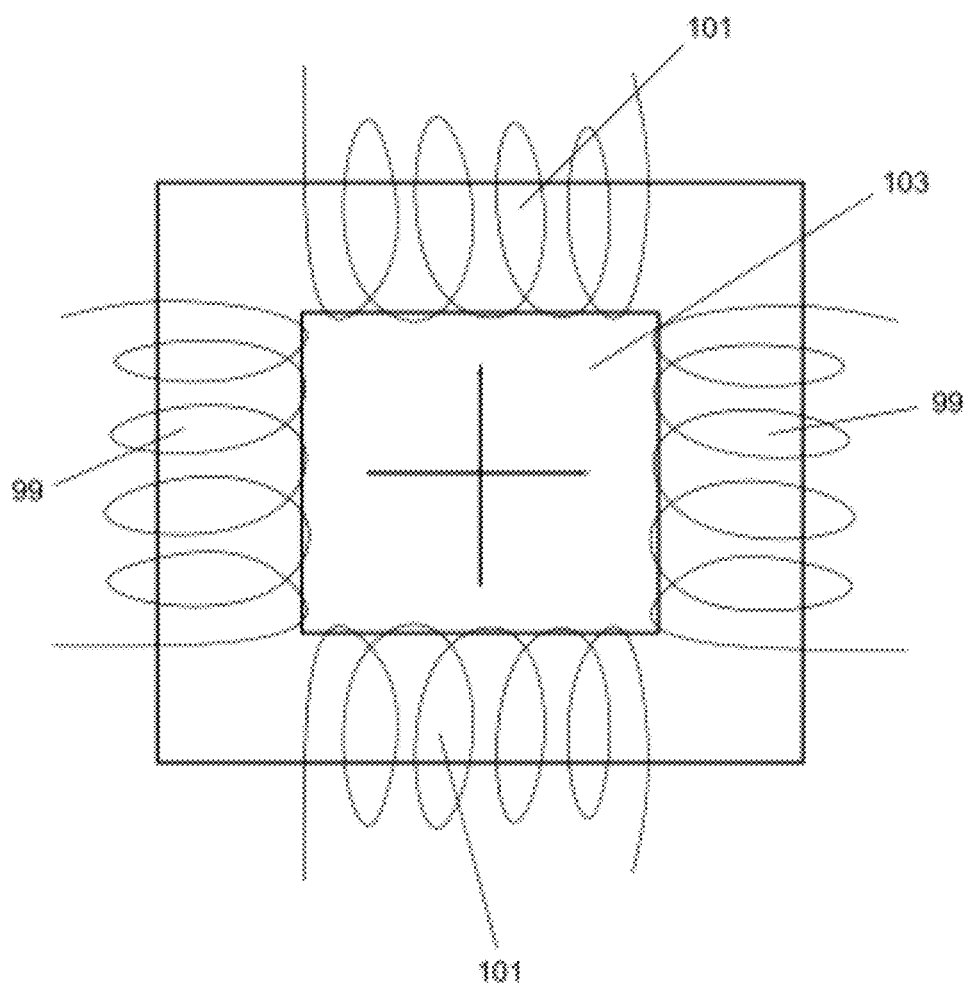
FIG. 9 is an exemplary illustration of the two planes scanning magnet of the same gantry of the present invention.

Referring now to FIG. 9, illustrated generally is an exemplary embodiment of a scanning magnet according to the present invention. The scanning magnet should move the beam fast along one of the transverse axis (horizontal or vertical), for different beam positions in the transverse plane. Scanning in one axis should be very fast, while requirement for the fast scanning in the other plane might not be necessary. The scanner in the opposite axis of the plane usually has to wait until the fast scanner passes many spots in its direction (±10 cm).

Figure 10A:
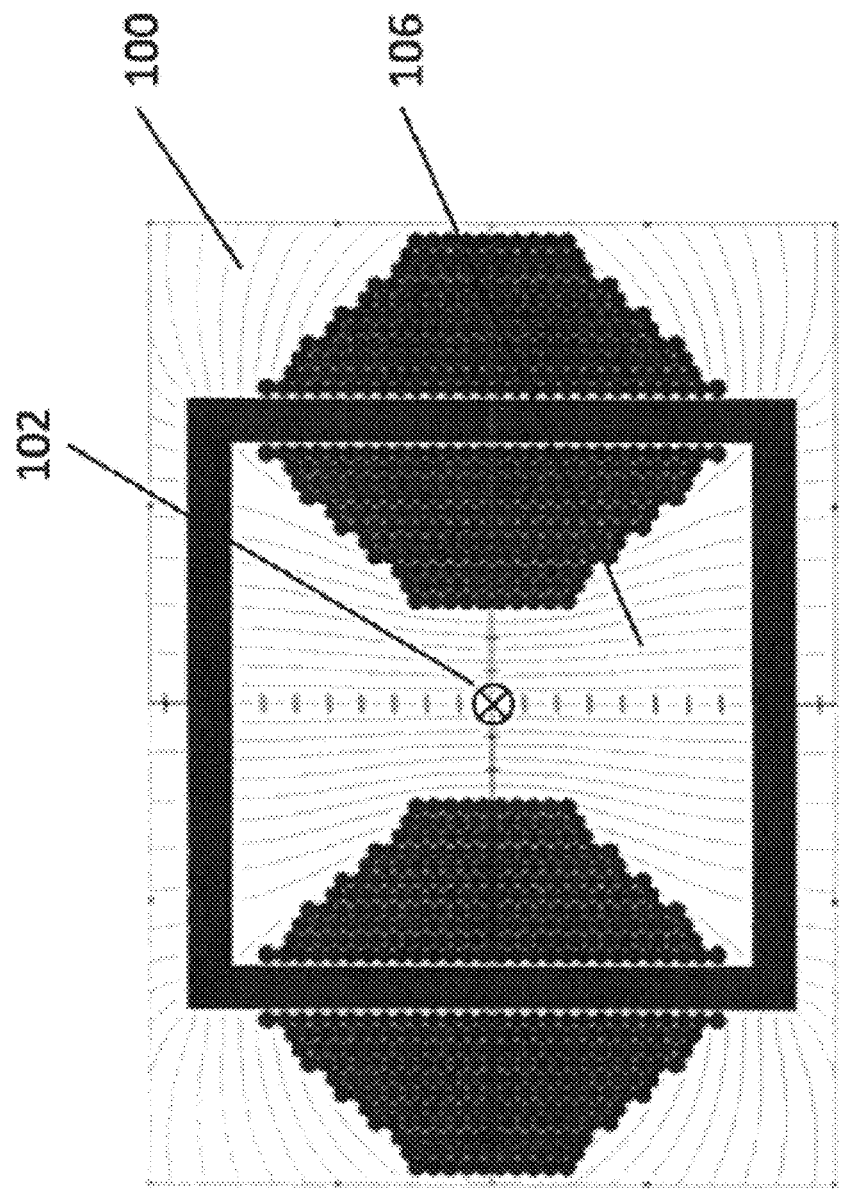
FIGS. 10A, 10B and 10C are exemplary illustrations of scanning magnets and magnetic fields within a scanning magnet according to the present invention.
Figure 10B:
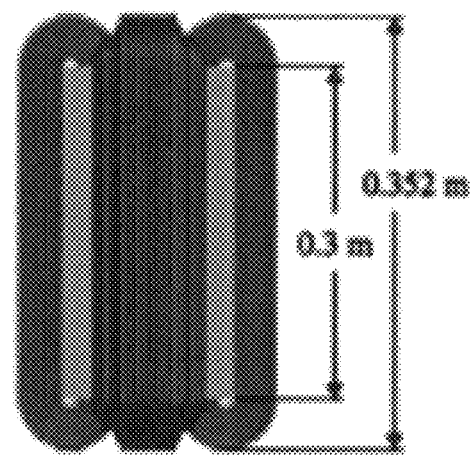
Figure 10C:
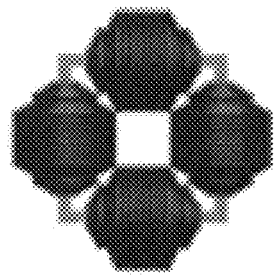

In accordance with that principle, referring to FIGS. 10A, 10B and 10C, a scanning magnet is shown in FIG. 10A where only copper coils 100 for the horizontal scanning are shown. The magnetic field lines are perpendicular to the horizontal axis, so the magnetic field B direction is either in an up-down direction or a down-up direction. The particles enter, with a speed v, into the aperture scanning magnet section, or ASMS, 102 perpendicularly. The Lawrence force bends ions in the down-up magnetic field direction into the right, or to the left for the direction of the magnetic field up-down, respectively. There are additional coils added to the magnetic steel, for banding in the vertical plane, as shown in FIGS. 10B and 10C. Typically, after review of the following design, a first scanning magnet will have a smaller aperture for the beam to travel through, while a second scanning magnet will have a larger aperture, which will be used to control the beam just prior to delivery. The magnet field lines 106 demonstrate the magnetic flux that is used to direct the ion to a specific path.

Although the present invention has been described in detail with reference to certain exemplary embodiments thereof, other versions are possible. For example, this invention maybe used with other radiotherapy devices, or may be used for scanning or imaging other than patients. Therefore, the spirit and scope of the appended claims should not be limited to the description of the preferred versions contained herein.

The invention claimed is:

1. A transport system for particle beam delivery, comprising:

a beam tube to deliver a particle beam to a patient, the beam tube defining a particle beam path to transport the particle beam from a particle beam entry point at which the particle beam enters the beam tube to a particle beam exit point at which the particle beam exits the beam tube;

a transfer system including a plurality of transfer magnets sequentially arranged along a portion of the beam tube to transfer the particle beam from the particle beam entry point through the beam tube along the particle beam path;

a bending and focusing system arranged along a portion of the beam tube after the portion of the beam tube along which the plurality of transfer magnets of the transfer system is arranged, the bending and focusing system including a plurality of combined function magnets to bend and focus the particle beam being transported through the beam tube along the particle beam path by providing a magnetic field that includes a combination of a bending dipole field with a focusing or defocusing quadrupole field; and a scanning system including a plurality of scanning magnets arranged along a portion of the beam tube after the portion of the beam tube along which the plurality of combined function magnets of the bending and focusing system is arranged and before the particle beam exit point, the plurality of scanning magnets being controlled to selectively vary a beam offset of the particle beam to deliver the particle beam of a corresponding transverse offset from the particle beam exit point to the patient.

2. The transport system as defined in claim 1, wherein the scanning system of the plurality of scanning magnets comprises a first scanning magnet and a second scanning magnet.

3. The transport system as defined in claim 2, wherein the first scanning magnet has an aperture that is smaller than an aperture of the second scanning magnet.

4. The transport system as defined in claim 3, wherein the second scanning magnet delivers the particle beam in a direction normal to the patient.

5. The transport system as defined in claim 1, wherein the bending and focusing system comprises a set of three combined function magnets for defining a beam size of the particle beam delivered to the patient.

6. The transport system as defined in claim 1, wherein
the scanning system of a plurality of scanning magnets comprises a first scanning magnet and a second scanning magnet, the first scanning magnet having an aperture smaller than an aperture of the second scanning magnet, and
the second scanning magnet having the aperture larger than the aperture of the first scanning magnet bends the particle beam in a direction normal to the patient.

7. The transport system as defined in claim 1, wherein the transfer system, the bending and focusing system, and the scanning system include superconducting magnets.

8. The transport system as defined in claim 7, wherein the particle beam comprises carbon ions or protons.

9. A method for delivering a particle beam to a patient to be treated by the particle beam, comprising:
transporting a particle beam through a beam tube from a particle beam entry point at which the particle beam enters the beam tube to a particle beam exit point at which the particle beam exits the beam tube, the beam tube defining a particle beam path:
transferring the particle beam from the particle beam entry point through the beam tube along the particle beam path by a plurality of transfer magnets sequentially arranged along a portion of the beam tube;
bending and focusing the particle beam being transported through the beam tube, after the particle beam has passed through the portion of the beam tube along which the plurality of transfer magnets is sequentially arranged, by a plurality of combined function magnets arranged along a portion of the beam tube after the portion of the beam tube along which the plurality of transfer magnets is sequentially arranged, the plurality of combined function magnets providing a magnetic field that includes a combination of a bending magnetic field with a focusing or a defocusing magnetic field; and
selectively controlling a beam offset of the particle beam being transported through the beam tube along the particle beam path, after the bending and focusing of the particle beam, by a plurality of scanning magnets arranged along a portion of the beam tube after the portion of the beam tube along which the plurality of combined function magnets is arranged and before the particle beam exit point, to selectively vary the beam offset of the particle beam to deliver the particle beam of a corresponding transverse offset from the beam tube at the particle beam exit point to a patient to be treated with the particle beam.

10. The method of claim 9, wherein
selectively controlling a beam offset of the particle beam comprises passing the particle beam through a first scanning magnet and a second scanning magnet, and
the first scanning magnet has an aperture smaller than an aperture of the second scanning magnet.

11. The method of claim 10, wherein the passing the particle beam through the larger aperture of the second scanning magnet delivers the particle beam in a direction normal to the patient.

12. The method of claim 9, wherein the plurality of transfer magnets focus the particle beam with a small dispersion function to provide a reduction in a beam size of the particle beam and a corresponding reduction in a size of the transfer magnets.

13. The method of claim 12, wherein the plurality of combined function magnets provides a magnetic field including a combination of a bending dipole field with a focusing or defocusing quadrupole field.

14. The method of claim 9, wherein the plurality of combined function magnets provides a magnetic field including a combination of a bending dipole field with a focusing or defocusing quadrupole field.

15. A particle beam therapy system, comprising:
a beam tube to deliver a particle beam to a patient, the beam tube defining a particle beam path to transport the particle beam from a particle beam entry point at which the particle beam enters the beam tube to a particle beam exit point at which the particle beam exits the beam tube;
a transfer system including a plurality of transfer magnets sequentially arranged along a portion of the beam tube to transfer the particle beam from the particle beam entry point through the beam tube along the particle beam path;
a bending and focusing system arranged along a portion of the beam tube after the portion of the beam tube along which the plurality of transfer magnets of the transfer system is arranged, the bending and focusing system including a plurality of combined function magnets to bend and focus the particle beam being transported through the beam tube along the particle beam path; and
a scanning system including a plurality of scanning magnets arranged along a portion of the beam tube after the portion of the beam tube along which the plurality of combined function magnets of the bending and focusing system is arranged and before the particle beam exit point, the plurality of scanning magnets being controlled to selectively vary a beam offset of the particle beam to deliver the particle beam of a corresponding transverse offset from the particle beam exit point to the patient.

16. The particle beam therapy system as defined in claim 15, wherein
the plurality of transfer magnets focus the particle beam with a small dispersion function to provide a reduction in a beam size of the particle beam and a corresponding reduction in a size of the transfer magnets, and
the plurality of combined function magnets provides a magnetic field including a combination of a bending dipole field with a focusing or defocusing quadrupole field.

17. The particle beam therapy system as defined in claim 15, wherein the bending and focusing system of magnets includes three combined function magnets.

18. The particle beam therapy system as defined in claim 15, wherein the scanning system of the plurality of scanning magnets delivers the particle beam from the beam exit point in a direction normal to the patient.

19. The particle beam therapy system as defined in claim 15, wherein the plurality of scanning magnets comprises a first scanning magnet and a second scanning magnet.

20. The particle beam therapy system as defined in claim 19, wherein
the first scanning magnet has an aperture smaller than an aperture of the second scanning magnet, and
the second scanning magnet having the aperture larger than the aperture of the first scanning magnet delivers the particle beam in a direction normal to the patient.

\* \* \* \* \*